(12) United States Patent
Mytych et al.

(10) Patent No.: US 6,964,843 B1
(45) Date of Patent: Nov. 15, 2005

(54) METHODS AND REAGENTS FOR THE DETECTION OF ANTIBODIES TO ADENOVIRUS

(75) Inventors: Daniel T. Mytych, Thousand Oaks, CA (US); Steven J. Swanson, Moorpark, CA (US)

(73) Assignee: Schering Corporation, Kenilworth, NJ (US)

( * ) Notice: Subject to any disclaimer, the term of this patent is extended or adjusted under 35 U.S.C. 154(b) by 733 days.

(21) Appl. No.: 09/643,458

(22) Filed: Aug. 22, 2000

Related U.S. Application Data
(60) Provisional application No. 60/150,622, filed on Aug. 25, 1999.

(51) Int. Cl.$^7$ .......................... C12Q 1/24; C12Q 1/25; A61K 39/235; G01N 33/351; G01N 33/352
(52) U.S. Cl. ..................... 435/5; 435/7.1; 435/7.92; 424/185.1; 424/186.1; 424/233.1
(58) Field of Search ........................... 435/5, 7.1, 7.92; 424/185.1, 186.1, 233.1

(56) References Cited

U.S. PATENT DOCUMENTS
5,424,218 A * 6/1995 Miljanich et al. ........... 436/503

OTHER PUBLICATIONS

Roder et al., "Biomolecular Interaction Analysis. Strategies for Antibody and Antigen Charaterization", Methods In Molecular Medicine, vol. 13: Molecular Diagnosis of Infectious Diseases, pp. 531–554.*
Zeng et al., "Analysis of Specific Interactions of Synthetic Glycopolypeptides Carrying N–Acetyllactosamine and Related Compounds with Lectins", Carbohydrate Research 312 (1998) 209–217.*
Karlsson et al., "Surface Plasmon Resonance Detection and Multispot Sensing for Direct Monitoring of Interactions Involving Low–Molecular–Weight Analytes and for Determination of Low Affinities", Analytical Biochemistry 228 (1995) 274–280.*
Wong et al., "Validation parameters for a novel biosensor assay which simultaneously measures serum concentrations of a humanized monoclonal antibody and detects induced antibodies", Journal of Immunological Methods 209 (1997) 1–15.*
Crawford–Miksza et al., "Analysis of 15 Adenovirus Hexon Proteins Reveals the Location and Structure of Seven Hypervariable Regions Containing Serotype–Specific Residues", Journal of Virology 70:3 (Mar. 1996) 1836–1844.*
Jonsson et al., "Introducing a biosensor based system for real–time biospecific interaction analysis", Pharmacia Biosensor AB 1–9.*
Toogood et al., "Antipeptide antisera define neutralizing epitopes on the adenovirus hexon", Journal of General Virology 73 (1992) 1429–1435.*
Kinloch et al., "Adenovirus Hexon. Sequence Comparison of Subgroup C serotypes 2 and 5", The Journal of Biological Chemistry 259:10 (May 25, 1984) pp. 6431–4346.*

\* cited by examiner

*Primary Examiner*—James Housel
*Assistant Examiner*—Bao Qun Li
(74) *Attorney, Agent, or Firm*—Nancy V. Connelly; Donald W. Wyatt

(57) ABSTRACT

The present invention provides methods and reagents for detecting antibodies to adenovirus. In a preferred embodiment, the present invention is useful for detecting antibodies to adenovirus serotype 5. In a further preferred embodiment, the present invention can be used in a biosensor-based assay. It is contemplated that the present invention is useful to detect antibodies for ascertaining adenovirus infection, evaluating patient response to gene therapy using adenovirus vectors, developing vaccines to adenovirus infection, developing therapeutics for inducing passive immunity to adenovirus infection, as well as other uses.

9 Claims, No Drawings

SEQUENCE LISTING

```
<160> NUMBER OF SEQ ID NOS: 16

<210> SEQ ID NO 1
<211> LENGTH: 32
<212> TYPE: PRT
<213> ORGANISM: artificial sequence
<220> FEATURE:
<223> OTHER INFORMATION: peptide for detection of adenovirus antibody
<220> FEATURE:
<221> NAME/KEY: MOD_RES
<222> LOCATION: 32
<223> OTHER INFORMATION: AMIDATION

<400> SEQUENCE: 1

Ala Ala Thr Ala Leu Glu Ile Asn Leu Glu Glu Asp Asp Asp Asn
1               5                   10                  15

Glu Asp Glu Val Asp Glu Gln Ala Glu Gln Gln Lys Thr His Val Phe
            20                  25                  30

<210> SEQ ID NO 2
<211> LENGTH: 13
<212> TYPE: PRT
```

```
<213> ORGANISM: artificial sequence
<220> FEATURE:
<223> OTHER INFORMATION: peptide for detection of adenovirus antibody
<220> FEATURE:
<221> NAME/KEY: MOD_RES
<222> LOCATION: 13
<223> OTHER INFORMATION: AMIDATION

<400> SEQUENCE: 2

Ile Gly Val Glu Gly Gln Thr Pro Lys Tyr Ala Asp Lys
1               5                   10

<210> SEQ ID NO 3
<211> LENGTH: 15
<212> TYPE: PRT
<213> ORGANISM: artificial sequence
<220> FEATURE:
<223> OTHER INFORMATION: peptide for detection of adenovirus antibody
<220> FEATURE:
<221> NAME/KEY: MOD_RES
<222> LOCATION: 15
<223> OTHER INFORMATION: AMIDATION

<400> SEQUENCE: 3

Tyr Glu Thr Glu Ile Asn His Ala Ala Gly Arg Val Leu Lys Lys
1               5                   10                  15

<210> SEQ ID NO 4
<211> LENGTH: 14
<212> TYPE: PRT
<213> ORGANISM: artificial sequence
<220> FEATURE:
<223> OTHER INFORMATION: peptide of detection of adenovirus antibody
<220> FEATURE:
<221> NAME/KEY: MOD_RES
<222> LOCATION: 14
<223> OTHER INFORMATION: AMIDATION

<400> SEQUENCE: 4

Gly Ile Leu Val Lys Gln Gln Asn Gly Lys Leu Glu Ser Gln
1               5                   10

<210> SEQ ID NO 5
<211> LENGTH: 17
<212> TYPE: PRT
<213> ORGANISM: artificial sequence
<220> FEATURE:
<223> OTHER INFORMATION: peptide for detection of adenovirus antibody
<220> FEATURE:
<221> NAME/KEY: MOD_RES
<222> LOCATION: 17
<223> OTHER INFORMATION: AMIDATION

<400> SEQUENCE: 5

Ser Thr Thr Glu Ala Thr Ala Gly Asn Gly Asp Asn Leu Thr Pro Lys
1               5                   10                  15
Val

<210> SEQ ID NO 6
<211> LENGTH: 14
<212> TYPE: PRT
<213> ORGANISM: artificial sequence
<220> FEATURE:
<223> OTHER INFORMATION: peptide of detection of adenovirus antibody
<220> FEATURE:
<221> NAME/KEY: MOD_RES
<222> LOCATION: 14
<223> OTHER INFORMATION: AMIDATION

<400> SEQUENCE: 6
```

Met Pro Thr Ile Lys Glu Gly Asn Ser Arg Glu Leu Met Gly
1               5                   10

<210> SEQ ID NO 7
<211> LENGTH: 30
<212> TYPE: PRT
<213> ORGANISM: artificial sequence
<220> FEATURE:
<223> OTHER INFORMATION: peptide of detection of adenovirus antibody
<220> FEATURE:
<221> NAME/KEY: MOD_RES
<222> LOCATION: 30
<223> OTHER INFORMATION: AMIDATION

<400> SEQUENCE: 7

Val Ile Asn Thr Glu Thr Leu Thr Lys Val Lys Pro Lys Thr Gly Gln
1               5                   10                  15

Glu Asn Gly Trp Glu Lys Asp Ala Thr Glu Phe Ser Asp Lys
            20                  25                  30

<210> SEQ ID NO 8
<211> LENGTH: 5
<212> TYPE: PRT
<213> ORGANISM: artificial sequence
<220> FEATURE:
<223> OTHER INFORMATION: leading sequence

<400> SEQUENCE: 8

Cys Lys Gly Lys Gly
1               5

<210> SEQ ID NO 9
<211> LENGTH: 37
<212> TYPE: PRT
<213> ORGANISM: artificial sequence
<220> FEATURE:
<223> OTHER INFORMATION: peptide for detection of adenovirus antibody
<220> FEATURE:
<221> NAME/KEY: MOD_RES
<222> LOCATION: 37
<223> OTHER INFORMATION: AMIDATION

<400> SEQUENCE: 9

Cys Lys Gly Lys Gly Ala Ala Thr Ala Leu Glu Ile Asn Leu Glu Glu
1               5                   10                  15

Glu Asp Asp Asp Asn Glu Asp Glu Val Asp Glu Gln Ala Glu Gln Gln
            20                  25                  30

Lys Thr His Val Phe
            35

<210> SEQ ID NO 10
<211> LENGTH: 18
<212> TYPE: PRT
<213> ORGANISM: artificial sequence
<220> FEATURE:
<223> OTHER INFORMATION: peptide for detection of adenovirus antibody
<220> FEATURE:
<221> NAME/KEY: MOD_RES
<222> LOCATION: 18
<223> OTHER INFORMATION: AMIDATION

<400> SEQUENCE: 10

Cys Lys Gly Lys Gly Ile Gly Val Glu Gly Gln Thr Pro Lys Tyr Ala
1               5                   10                  15

Asp Lys

```
<210> SEQ ID NO 11
<211> LENGTH: 20
<212> TYPE: PRT
<213> ORGANISM: artificial sequence
<220> FEATURE:
<223> OTHER INFORMATION: peptide for detection of adenovirus antibody
<220> FEATURE:
<221> NAME/KEY: MOD_RES
<222> LOCATION: 20
<223> OTHER INFORMATION: AMIDATION

<400> SEQUENCE: 11

Cys Lys Gly Lys Gly Tyr Glu Thr Glu Ile Asn His Ala Ala Gly Arg
 1               5                  10                  15

Val Leu Lys Lys
         20

<210> SEQ ID NO 12
<211> LENGTH: 19
<212> TYPE: PRT
<213> ORGANISM: artificial sequence
<220> FEATURE:
<223> OTHER INFORMATION: peptide for detection of adenovirus antibody
<220> FEATURE:
<221> NAME/KEY: MOD_RES
<222> LOCATION: 19
<223> OTHER INFORMATION: AMIDATION

<400> SEQUENCE: 12

Cys Lys Gly Lys Gly Gly Ile Leu Val Lys Gln Gln Asn Gly Lys Leu
 1               5                  10                  15

Glu Ser Gln

<210> SEQ ID NO 13
<211> LENGTH: 22
<212> TYPE: PRT
<213> ORGANISM: artificial sequence
<220> FEATURE:
<223> OTHER INFORMATION: peptide of detection of adenovirus antibody
<220> FEATURE:
<221> NAME/KEY: MOD_RES
<222> LOCATION: 22
<223> OTHER INFORMATION: AMIDATION

<400> SEQUENCE: 13

Cys Lys Gly Lys Gly Ser Thr Thr Glu Ala Thr Ala Gly Asn Gly Asp
 1               5                  10                  15

Asn Leu Thr Pro Lys Val
         20

<210> SEQ ID NO 14
<211> LENGTH: 19
<212> TYPE: PRT
<213> ORGANISM: artificial sequence
<220> FEATURE:
<223> OTHER INFORMATION: peptide of detection of adenovirus antibody
<220> FEATURE:
<221> NAME/KEY: MOD_RES
<222> LOCATION: 19
<223> OTHER INFORMATION: AMIDATION

<400> SEQUENCE: 14

Cys Lys Gly Lys Gly Met Pro Thr Ile Lys Glu Gly Asn Ser Arg Glu
 1               5                  10                  15

Leu Met Gly
```

```
<210> SEQ ID NO 15
<211> LENGTH: 35
<212> TYPE: PRT
<213> ORGANISM: artificial sequence
<220> FEATURE:
<223> OTHER INFORMATION: peptide of detection of adenovirus antibody
<220> FEATURE:
<221> NAME/KEY: MOD_RES
<222> LOCATION: 35
<223> OTHER INFORMATION: AMIDATION

<400> SEQUENCE: 15

Cys Lys Gly Lys Gly Val Ile Asn Thr Glu Thr Leu Thr Lys Val Lys
1               5                   10                  15

Pro Lys Thr Gly Gln Glu Asn Gly Trp Glu Lys Asp Ala Thr Glu Phe
            20                  25                  30

Ser Asp Lys
        35

<210> SEQ ID NO 16
<211> LENGTH: 4
<212> TYPE: PRT
<213> ORGANISM: artificial sequence
<220> FEATURE:
<223> OTHER INFORMATION: leading sequence

<400> SEQUENCE: 16

Lys Gly Lys Gly
1
```

METHODS AND REAGENTS FOR THE DETECTION OF ANTIBODIES TO ADENOVIRUS

This application claims the benefit of U.S. Provisional Application No. 60/150,622 filed Aug. 25, 1999.

Throughout this disclosure, various publications, patents and patent applications are referenced. The disclosures of these publications, patents and patent applications are herein incorporated by reference.

FIELD OF THE INVENTION

The present invention pertains to methods and reagents for the detection of antibodies that bind to adenovirus. In preferred embodiments, the present invention is directed to detecting antibodies to adenovirus 5. The usefulness of the present invention includes, but is not limited to, identifying patients likely to have an immune response to gene therapy, vaccines to prevent or treat adenovirus infection, therapeutics to induce passive immunity to adenovirus infection and the like.

BACKGROUND

Prospects for gene therapy to correct genetic disease or to deliver therapeutic molecules depend on the development of gene transfer vehicles that can safely deliver exogenous nucleic acid to a recipient cell. To date, most efforts have focused on the use of virus-derived vectors that carry a heterologous gene (transgene) in order to exploit the natural ability of a virus to deliver genomic content to a target cell.

For example, despite their reputation as major pathogenic agents that lead to numerous infectious diseases, adenoviruses (and particularly, replication-deficient adenoviruses) have attracted considerable recognition as highly effective viral vectors for gene therapy. Adenoviral vectors offer exciting possibilities based on their high efficiency of gene transfer, substantial carrying capacity, and ability to infect a wide range of cell types. Due to these desirable properties of adenoviruses, recombinant adenoviral vectors have been used for the cell-targeted transfer of one or more recombinant genes to diseased cells or tissue in need of treatment. In fact, adenovirus-based vectors offer several advantages, including tropism for both dividing and non-dividing cells, minimal pathogenic potential, ability to prepare vector stocks at high titer, and the potential to carry large DNA inserts. To date, genes that have been expressed by adenoviral vectors include p53, dystrophin, erythropoietin, ornithine transcarbamylase, adenosine deaminase, interleukin-2 and α-antitrypsin. Examples of adenovirus vectors can be found in U.S. Pat. No. 5,585,362 to Wilson et al., U.S. Pat. No. 5,824,544 to Armentano et al., and U.S. Pat. No. 5,846,782 to Wickham et al.

One barrier to successful gene transfer by viral vectors to patient hosts is the immune response of the host to the introduction of the virus. In terms of the general structure of an adenovirus, under the electron microscope, an adenovirus particle resembles a space capsule having protruding antennae. The viral capsid comprises at least six different polypeptides, including hexon, base and fiber proteins. The fiber, together with the hexon (Crawford-Miksza, L. and Schnurr, D. P., J. Virology, March 1996, pp. 1836–1844), determine the serotype specificity of the virus, and also comprise the main antigenic determinants of the virus.

This ability of adenoviral fiber and hexon protein to act as targets for a host immune response hamper attempts at adenoviral-mediated gene therapy. Namely, following adenoviral vector re-administration to prolong the therapeutic response, neutralizing antibodies develop against the adenoviral fiber and/or hexon proteins, thus circumventing adenoviral gene delivery to host cells. As the therapy is expensive, it is extremely wasteful to utilize a viral vector for gene therapy in a patient host that will mount an immune response to the vector.

What is needed is an efficient method of determining the likelihood that a patient host's immune system will interfere with intended gene therapy using viral vectors.

SUMMARY OF THE INVENTION

The present invention provides methods and reagents for detecting antibodies capable of binding to adenovirus. In one embodiment, the present invention provides a method for detecting antibodies capable of binding to adenovirus comprising: a) immobilization of one or more peptides capable of being bound by an anti-adenovirus antibody directly onto a flowcell of a sensorchip in a biosensor, b) obtaining a serum sample from a patient to be tested and contacting said serum sample with the immobilized peptide, and c) measuring binding of antibodies to the immobilized peptide by means of the biosensor. In preferred embodiments, more than one peptide is utilized and are directly immobilized, each on its own separate flowcell.

In another embodiment, the present invention provides a method for detecting antibodies capable of binding to adenovirus, comprising a peptide selected from the group consisting of:

AATALEINLEEEDDDNEDEVDEQAEQQKTHVF-Amide (SEQ ID NO: 1), IGVEGQTPKYADK-Amide (SEQ ID NO:2), YETEINHAAGRVLKK-Amide (SEQ ID NO:3), GILVKQQNGKLESQ-Amide (SEQ ID NO:4), STTEATAGNGDNLTPKV-Amide (SEQ ID NO:5), MPTIKEGNSRELMG-Amide (SEQ ID NO:6), VINTETLTKVKPKTGQENGWEKDATEFSDK-Amide (SEQ ID NO:7), or peptides having substantial sequence identity thereto. While not limited to a specific method of detection, in one embodiment the method of detecting comprises an ELISA system.

In yet another embodiment, the present invention provides a composition of matter comprising CKGKG (SEQ ID NO:8) or a peptide having substantial sequence identity thereto, and their use in a biosensor based assay to detect antibodies.

While certain embodiments of the present invention is not limited to specific peptides, in preferred embodiments the peptide is capable of being bound by antibodies specific to adenovirus 5. Examples of such peptides include those described above, as well as the following: CKGKGAATALEINLEEEDDDNEDEVDEQAEQQKTH-VF-Amide (SEQ ID NO:9). CKGKGIGVEGQTPKYADK-Amide (SEQ ID NO: 10), CKGKGYETEINHAA-GRVLKK-Amide (SEQ ID NO: 11), CKGKGGIL-VKQQNGKLESQ-Amide (SEQ ID NO: 12), CKGKGSTTEATAGNGDNLTPKV-Amide (SEQ ID NO: 13), CKGKGMPTIKEGNSRELMG-Amide (SEQ ID NO: 14), CKGKGVINTETLTKVKPKTGQENGWEKDATEFSDK-Amide (SEQ ID NO: 15), or peptides having substantial sequence identity thereto.

In another embodiment, the present invention encompasses peptides that correspond to family reactive determinants of hexon and penton. This includes peptides that cross-react with similar antigens of other viral vectors.

The present invention is also not limited by the sample to be analyzed for antibodies. In one embodiment, the sample is human serum. In a preferred embodiment, the serum sample is simultaneously contacting with a plurality of immobilized peptides. Likewise, it is preferred that when more than one peptide is used, at least one of the plurality of peptides is capable of being bound by antibodies specific to adenovirus 5.

While not limited by the desired results of an assay, in preferred embodiments, the amount of antibody that binds to each peptide is directly proportional to the response units that are reported by the biosensor.

Finally, although the present invention is not limited by the equipment used; in a preferred embodiment, it is a BIACORE 2000™ biosensor. (The above sequences are listed using standard one-letter amino acid symbols; see e.g., Lehninger, *Principles of Biochemistry*, Worth Publishers, Inc. 6$^{th}$ Ed. 1988, p. 96).

Definitions

An "antibody" includes, but is not limited to, immunoglobulin molecules and immunologically active portions of immunoglobulin molecules such as portions containing a paratope (i.e., an antigen binding site). In particular, an antibody preferably can be a bispecific antibody, i.e., having one paratope directed to an epitope of the chimeric fiber protein, and another paratope directed to an epitope of a cell surface-binding site.

A "vector" according to the invention is a vehicle for gene transfer, as that term is understood by those skilled in the art. Three types of vectors encompassed by the invention are plasmids, phages, and viruses. Plasmids, phages, and viruses can be transferred to a cell in their nucleic acid form (e.g., via transfection). In comparison, phages and viruses also can be transferred with the nucleic acid in a "capsular" form. Hence, the vectors (e.g., capsular form) that can be employed for gene transfer are referred to herein generally as "vectors", with nucleic acid forms being referred to more particularly as "transfer vectors". However, transfer vectors also are vectors within the context of the invention.

"Substantial sequence identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more. Preferably, residue positions that are not identical differ by conservative amino acid substitutions. For example, the substitution of amino acids having similar chemical properties such as charge or polarity are not likely to effect the properties of a protein. Examples include glutamine for asparagine or glutamic acid for aspartic acid. In addition, substantial sequence identity encompasses amino acids or chemicals that create a similar structure. For example, linear, cyclic, or constrained peptides.

DETAILED DESCRIPTION OF THE INVENTION

The present invention provides methods and reagents for detecting antibodies to adenovirus. In one embodiment, the present invention provides peptides for detecting anti-adenovirus antibodies. In another embodiment, the present invention provides novel peptides for detecting anti-adenovirus antibodies in a biosensor-based assay. The present invention is not limited to the serotype of the adenovirus capable of being bound by the antibodies detected. In a preferred embodiment, however, the serotype is adenovirus 5 (AV5).

The present invention is also not limited to the specific type of assay used to detect the anti-adenovirus antibodies.

In one embodiment, the present invention contemplates the use of an enzyme-linked immunosorbant assays (ELISA). An ELISA assay, in general, is performed by binding a reference reagent (antigen) to a solid phase support. Samples to be tested are mixed with a labeled reagent, then reacted with the bound reference reagent. The reagents then undergo a series of dilution, incubation, and washing steps in order to separate bound and free reagents. The process concludes with a detection step, compatible with the type of label used, designed to indirectly measure the amount of antibody (or antigen) in the samples tested. For example, a commercially available enzyme-linked immunosorbant assay (ELISA) to detect enteric adenoviruses based on a polyclonal antibody to enteric adenovirus hexon protein is available (Adeno-Type 40/41 EIA, Cambridge Bioscience, Cambridge, Mass.).

In another embodiment, the present invention contemplates the use of ORIGEN electrochemilumninescence (ECL) detection system (Igen, Gaithersburg, Md.). Briefly, the ECL system utilizes strepavidin-coated paramagnetic beads to capture and detect immune complexes formed between antigen bound to a biotin-conjugated antibody.

The present invention also contemplates the use of a biosensor-based assay. The biosensor used in the present invention is preferably a BIACORE 2000™ from Pharmacia (Uppsalla, Sweden). The BIACORE 2000™ operates on a principle of surface plasmon resonance and allows for high throughput analyses. (See, e.g., Hodgson, Bio/Technology vol. 12, January 1994 for a review of biosensors). Other biosensors, e.g., a BIACORE™ X (Biacore 1000™; Biacore 3000™ T) from Pharmacia or an IAsys biosensor from Fisons, could be used in connection with the present invention. In analyzing the results of the assay, it is preferred that the amount of antibody that binds to each peptide is directly proportional to the biosensor signal (e.g. the response units that are reported by the BIACORE 2000™ biosensor).

Among other advantages, use of a biosensor assay in the present invention provides an assay that is suited for detecting lower affinity antibodies (Obenauer-Kutner et al., Journal of Immunological Methods, 1997, 206:25–33; Swanson et al., Dev. Biol. Stand. Basel, Karger, 1999, 97:135–147). Methods employing ELISAs have difficulty in this regard because ELISAs require multiple incubation steps followed by wash cycles during which lower affinity antibodies can wash away. There is also a need for an assay that is less labor intensive than the methods utilizing an ELISA format. Finally, there is a need to significantly reduce analysis time, preferably to less than 10 minutes/sample, to allow for high throughput analyses. As mentioned above, ELISAs require multiple incubation steps followed by wash cycles, and therefore the materials used in the assay cannot be regenerated for analysis of subsequent samples.

While the present invention is not limited to specific peptides for detection of adenovirus, preferred peptides for use in the methods of the present invention are comprised of one or more of the sequences below (or peptides having substantial sequence identity thereto):

a) Peptide SEQ ID NO: 1 (HVR1 of AV5), AATALEINLEEEDDDNEDEVDEQAEQQKTHVF-Amide;

b) Peptide SEQ ID NO: 2 (HVR2 of AV5), IGVEGQTPKYADK-Amide c) Peptide SEQ ID NO: 3 (HVR3 of AV5), YETEINHAAGRVLKK-Amide d) Peptide SEQ ID NO: 4 (HVR4 of AV5), GILVKQQNGKLESQ-Amide e) Peptide SEQ ID NO: 5 (HVR5 of AV5), STTEATAGNGDNLTPKV-Amide f) Peptide SEQ ID NO: 6 (HVR6 of AV5), MPTIKEGNSRELMG-Amide g) Peptide SEQ ID NO: 7 (HVR7 of AV5), VINTETLTKVKPKTGQENGWEKDATEFSDK-Amide The above sequences are described in Crawford-Miksza et al., J. Vir. 70:1836, 1996, Toogood et al., J. Gen. Vir. 73:1429, 1992, and Kinloch et al., J. Biol. Chem 259:6431, 1984. These peptides, however, are reported as part of conformational proteins. Surprisingly, peptides HVR1 (SEQ ID NO: 1) and HVR6 (SEQ ID NO: 6) have been identified as part of internalized loops within the hexon protein that are not even exposed to the external surface (Haase & Pereira, J. Immunol. 108:633–636, 1972; Kjellen & Pereira, J. Gen. Vir. 2:177–185, 1968; Mautner & Wilcox, J. Gen Vir. 25:325–336, 1974; Norrby, Virology 37:565–576, 1969; Wilcox & Mautner, J. Immunol. 116:19–24, 1976). It would be expected, therefore, that if these peptides are suitable as targets for antibody binding, that the target of antibody binding is part of the protein's overall secondary and tertiary structure. As such, it is surprising that these short linear peptides, even within the internal loop, are suitable for detecting neutralizing viral antibodies. Furthermore, it is surprising to find serotype-specificity within peptides that include conserved sequences between serotypes.

When a peptide is used in a biosensor-based assay, it is preferred that a positively charged leader sequence be added next to a cysteine at the beginning of the peptide. This leader sequence interacts with the net negatively charged solid support of the biosensor system to enhance the immobilization of the peptide to the carboxymethyl dextran support surface. While not limited to a particular leading sequence, the first position must be cysteine (C) and the second position can be either lysine (K), arginine (R) or histidine (H), in a preferred embodiment, the leading sequence is CKGKG (SEQ ID NO: 8) (or peptides having substantial sequence identity thereto). This results in preferred peptides for use in a biosensor-based assay of (or peptides having substantial sequence identity thereto):

a) Peptide SEQ ID NO: 9 (HVR1 of AV5), CKGKGAATALEINLEEEDDDNEDEVDEQAEQQ-KTHVF-Amide;

b) Peptide SEQ ID NO: 10 (HVR2 of AV5), CKGKGIGVEGQTPKYADK-Amide c) Peptide SEQ ID NO: 11 (HVR3 of AV5), CKGKGYETEINHAAGRVLKK-Amide d) Peptide SEQ ID NO: 12 (HVR4 of AV5), CKGKGGILVKQQNGKLESQ-Amide e) Peptide SEQ ID NO: 13 (HVR5 of AV5), CKGKGSTTEATAGNGDNLTPKV-Amide f) Peptide SEQ ID NO: 14 (HVR6 of AV5), CKGKGMPTIKEGNSRELMG-Amide g) Peptide SEQ ID NO: 15 (HVR7 of AV5), CKGKGVINTETLTKVKPKTGQENGWEKDATEF-SDK-Amide When viral vectors are used to deliver gene therapy to a patient, the patient's immune reaction to the viral vector has a significant impact on the success of the therapy. For example, if a patient's immune system produces antibodies to the viral vector, the vector may be inactivated before it has properly delivered the therapeutic gene to the patient's cells.

Therefore, information about a patient's immune system and their antibodies against viral vectors is important. As an example, the level of high-concentration and/or high-affinity antibodies will have a direct impact on therapy. Moreover, the level of low-concentration and/or low-affinity antibodies is also an important factor to consider. Even though the amount of low-affinity antibodies may have a limited impact on the early stages of therapy, the data obtained may predict the development of increased quantities of antibodies or additional higher-affinity antibodies. Furthermore, the ratio of high-affinity to low-affinity antibodies is a valuable indicator that permits a medical provider to design and monitor a patient's therapy.

When the methods of the present invention are used, it is possible to detect low-concentration and/or low-affinity antibodies and differentiate them from the high concentration and/or high affinity antibodies. For example, using a system such as the BIACORE 2000™ to detect antibodies provides information on the amount of antibodies that can bind to an antigen, whether they are high- or low-affinity antibodies. This information can be compared to detection of antibodies under more stringent conditions (e.g., ELISA) that detect high-concentration and high-affinity antibodies. Thus an immune status profile can be generated that evaluates the amount of total antibodies, and whether they are of high-affinity and/or high concentration antibodies or low-affinity and/or low concentration antibodies.

The present invention further contemplates the preparation and use of a vaccine composition for the treatment of human adenovirus infection, including AV5. The preparation of such a vaccine is accomplished by utilization of at least one of the above peptides. This can be accomplished by utilization of at least one of the above peptides. This can be accomplished by genetic engineering of at least one of the above peptides and expressing at least one of these proteins in suitable vector/host cell systems such as bacteria, yeast or any other suitable vector/host system. In another embodiment, the present invention is directed to a Type II vaccine which is a combination of an inactivated adenovirus and at least one of the above-listed proteins.

By vaccine is meant an agent used to stimulate the immune system of a living organism so that protection against future harm is provided. A number of viral polypeptide preparations derived from viral coats or envelopes have been suggested as possible active components for vaccine compositions. For example, U.S. Pat. No. 4,470,967 describes vaccine preparations which are made by complexing viral polypeptide with a lectin, the latter element acting as adjuvant. A number of references, (e.g., 4,344,935 or 4,356,169 or Morein, et al., J. Gen. Virol., 64: 1557–1569, 1983), utilize a method of preparing parainfluenza glycoprotein compositions in which the viral glycoprotein HN and F are solubilized with a detergent, to extract them from the viral envelope, followed by some method of phase separation in order to remove the detergent and lipids. The latter procedures produce a glycoprotein subunit that is not only substantially detergent-free, but also lipid-free. The latter type of highly purified glycoprotein is considered the preferred type of active agent for potential use of commercial vaccine. An alternative approach is the synthesis of peptides for use as a vaccine.

Recombinant DNA techniques for the preparation of recombinant adenovirus peptides for use in the preparation of vaccines are sufficiently well known and widespread so as to be considered routine. In very general and broad terms, a method for use herein consists of transferring the genetic material, or more usually part of the genetic material, of one organism into a second organism so that the transferred genetic material becomes a permanent part of (recombines with) the genetic material of the organisms to which it is transferred.

This usually consists of first obtaining a small piece of DNA from the parent organism either from a plasmid or a parent chromosome. A plasmid (also called an extrachromosomal element) is a hereditary unit that is episomal, (i.e.—physically separate from the chromosome of the cell). The DNA may be of any size and is often obtained by the action of a restriction endonuclease enzyme that acts to split DNA molecules at specific base-pair sites. In the present invention an adenovirus peptide gene can be synthesized based upon the sequence of the protein to be expressed.

DNA pieces may be transferred into a host cell by various means. For example, transformation wherein naked DNA is internalized into a cell from the external environment, oftentimes through artificially induced disruption of the cell membrane (e.g. by introduction of various chemical agents, such as calcium ions or lipids, by application of electric current, by extreme temperature changes or by microinjection). Other methods of gene transfer such as transduction are also suitable, wherein DNA is packaged within a phage such as a cosmid or viral vector.

Once DNA is in the host cell, it may continue to exist as a separate piece (generally true of complete transmitted plasmids) or it may insert into the host cell chromosome and be reproduced together with the chromosome during cell division.

Administration of a vaccine contemplated by the present invention to the patient (human or animal) may be by any known or standard techniques. These include oral ingestion, intestinal intubation, or broncho-nasal spraying. Other methods of administration, such as intravenous injection, that allow the carrier microbe to reach the human or animal's bloodstream may be acceptable when the carrier microbe is replication deficient.

The amount required will vary with the antigenicity of the gene product and need only be an amount sufficient to induce an immune response typical of existing vaccines. Routine experimentation will easily establish the required amount. Typical initial dosages of vaccine could be about 0.001–100 mg antigen/kg body weight, with increasing amounts or multiple dosages used as needed to provide the desired level of protection.

The pharmaceutical carrier in which the vaccine is suspended or dissolved may be any solvent or solid that is non-toxic to the inoculated animal and compatible with the carrier organism or antigenic gene product. Suitable pharmaceutical carriers include liposomes and liquid carriers, such as normal saline and other non-toxic salts at or near physiological concentrations, and solid carriers, such as talc or sucrose. Adjuvants, such as Freund's adjuvant, complete or incomplete, may be added to enhance the antigenicity via the bronchial tubes, wherein the vaccine is suitably present in the form of an aerosol. Booster immunizations may be repeated numerous times with beneficial results.

In another aspect, the present invention relates to a method of treating infectious diseases caused by adenovirus infection by introducing passive immunity. Passive immunization, as defined herein, refers to resistance (e.g., temporary or sustained protection against infection) based on giving preformed antibodies to a patient from an in vivo or in vitro source. The main advantage of passive immunization is the prompt availability of large amounts of antibodies against human adenoviruses that can be identified as described in the above embodiment of the present invention.

For example, the present invention also encompasses antibodies, either monoclonal or polyclonal, that are identified using the systems described above and are useful in the therapeutic control of infection by adenoviruses. Said antibodies can be prepared by injecting mammalian species, e.g., human, horse, rabbit, sheep, mice, etc. with the peptides described above and then purifying said antibodies employing the detection systems contemplated and described herein.

In another embodiment, the present invention relates to the development of specific human or other eukaryotic (e.g., yeast, baculovirus, or Chinese hamster cells) polyclonal or monoclonal antibodies, as well as human-mouse chimeric polyclonal or monoclonal antibodies for administration in passive immunization against human adenoviruses. Such antibodies can be used as created in these systems, or they can be humanized. Methods of humanizing antibodies is described in U.S. Pat. No. 5,597,710 and 5,705,154 to Dalie et al., and U.S. Pat. No. 5,585,089 to Queen et al.

In addition, the generation of antibodies against the disclosed peptides can be used for commercial use. In one embodiment, these antibodies may be used as probes for various biochemical assays to detect adenovirus, more preferably AV5. In another embodiment, these antibodies may be used in kits to detect IR.

The present invention further contemplates the use peptides as probes to detect, by hybridization, cellular DNA from infected tissue (e.g. biopsy material) carrying integrated structural adenovirus DNA (i.e., DNA encoding one of the peptides described above). The probe can be DNA, cDNA, recombinant DNA or RNA.

In one particular embodiment of the present invention, the probes may be used for in situ hybridization. For example, patient specimens (tissue or tissue extracts) containing biopsy material are smeared onto a standard microscope slide, then fixed with an appropriate fixative. The DNA or RNA probe, which has been labeled (e.g. with biotin-avidin-enzyme) is added. The slide is then placed onto a heating block for one or two minutes to allow both the probe and the target nucleic acids to be separated from their complementary strand (if double stranded). Non-hybridized probe DNA or RNA is removed by gentle washing. After a suitable detection complex is added, hybridization is detected with a light microscope following formation of a colored compound. In other embodiments of the invention, the nucleic acid probe is labeled with a radioactive isotope or chemiluminescent tag. Alternatively, tissue to be tested may be lysed and DNA/RNA fixed to, nitrocellulose paper for example. Hybridization and DNA/RNA detection systems are well known in the art.

The following examples serve to illustrate certain preferred embodiments and aspects of the present invention and are not to be construed as limiting the scope thereof.

EXAMPLE 1

Materials and Methods 1.1 Equipment and Materials

BIACORE 2000™ biosensor instrument, amine coupling kit (NHS/EDC), PDEA, sensorchip CM5 (research grade) and P-20 surfactant were all obtained from BIACORE™, Uppsala, Sweden. The HEPES, NaCl, EDTA, Tris and 0.2 $\mu$M filters were obtained from Fisher Scientific, Springfield, N.J. The cysteine was obtained from Aldrich, Milwaukee, Wis.

The carboxymethyldextran was obtained from Fluka Chemical Corp., Ronkonkoma, N.Y.

1.2 Peptide Design

Each peptide was designed to contain an amino-terminal cysteine residue available for thiol-coupling followed by a KGKG linker to each of the seven hypervariable region (HVR) sequences of adenovirus type 5 hexon. The linker is designed to function as a spacer, as well as to provide a localized positive charge around the cysteine; thus facilitating thiol-coupling by attraction to the negatively charged sensorchip matrix. Each of the seven unique hypervariable sequences corresponding to adenovirus type 5 hexon was obtained from published sequences (Crawford-Miksza and Schnurr, 1996). These amino acid sequences are displayed according to the single letter code in Table 1. All seven linear peptides were synthesized by Research Genetics, Huntsville, Ala. and subsequently purified by HPLC to 85% purity.

1.3 Method of Biosensor Peptide Immobilization

Using the BIACORE 2000™, each of the seven peptides was immobilized onto a flow cell contained on a sensorchip. All peptides were diluted to 500 μg/ml. HVR 1, 2, 4, and 5 were diluted with 10 mM MES pH 5 and HVR 3, 6 and 7 were diluted in 10 mM sodium acetate buffer pH 4. Thiol-coupling chemistry was the standard coupling chemistry used for all peptides. The immobilization procedure was performed at a continuous flow rate of 5 μl per minute followed by the sequential injection of 20 μl of NHS/EDC, 40 μl of PDEA, 50 μl of peptide, and 40 μl of cysteine/1M NaCl. Each immobilized peptide was subsequently restored with a 5 μl pulse of 50 mM HCl between sample analyses.

1.4 Biosensor Analysis of Serum Samples:

Interaction of antibodies with Ad5 HVR peptides was monitored using a biosensor instrument (BIACORE 2000™). All BIACORE analysis was preformed at 25° C. using 10 mM HEPES buffered saline (HBS) with 0.05% P-20, and 3.4 mM EDTA (HBS) as the BIACORE running buffer. Specifically, the BIACORE running buffer consisted of 10 mM HEPES, 150 mM NaCl, 3.4 mM EDTA, and 0.05% P-20 pH 7.4. The HBS was filtered using 0.2 μm filter and subsequently de-gassed for 30 minutes at 25° C. Sample diluent contained HBS with 1 mg/ml soluble carboxymethyldextran (CM-D).

Serum sample analysis was performed by diluting serum 1:20 in HBS w/P-20 and CM-D, filtering through a 0.2 μm filter and then testing a 20 μL aliquot of each sample for binding to each of the immobilized peptides at a flow rate of 5 μl/minute. This protocol was followed for analysis of rats, rabbits and pigs immunized with rAd5, swine samples from a pre-clinical study as well as human samples from a clinical study. In addition, commercial type-specific pAb and mAbs, diluted based on antibody purity (antisera, purified IgG, etc.) were also tested for their reactivity to the HVR peptides. An automated method was run and data collected. The binding of each sample was recorded in response units (RU).

1.5 Affinity Purification of Anti-HVR1 Peptide Antibodies

HVR1 peptide was covalently coupled to a Sulfo-link agrose gel (Pierce, Rockford, Ill.). Approximately 2.5 ml of gel was equilibrated with binding buffer (50 mM Tris, 5 mM EDTA pH 8.5), centrifuged at 500×g for 5 minutes and supernatant subsequently decanted. A total of 2.8 mg of HVR1 peptide was mixed with 2.0 ml of gel in a total volume of 2 ml buffer for 2 hours at room temperature on a Nutator. (Note: Mixture is light-sensitive, therefore must be covered with foil). The slurry was centrifuged at 500×g for 5 minutes, and 2 ml of supernatant was removed. The gel was washed 5–6 times with 1 ml aliquots of binding buffer. The gel was then blocked by mixing it with 2 ml of 50 mM cysteine for 45 minutes at room temperature. The slurry was centrifuged, liquid decanted, and the gel equilibrated with 4 ml of binding buffer and stored at 4° C.

A 1.0 ml aliquot of serum from patient IK taken 14 days after receiving rAd5 was mixed with 1.0 ml of phosphate buffered saline (PBS), filtered through a 0.22 μm microcentrifuge tubes. The 2.0 ml of diluted serum sample was then added to 0.5 ml of gel and mixed overnight on a nutator at 4° C. The slurry was then transferred to a disposable column. The column containing the gel was then washed with 10 ml of PBS. Bound antibodies were then eluted by addition of 2.0 ml aliquots of 100 mM Glycine-HCL pH 2.8 and 0.5 ml fractions were collected. Each eluted fraction was neutralized by the addition of 12.5 μl of 2M Tris pH 11 to each fraction. All fractions were then dialyzed against 4 liters of PBS using 10 KD MWCO Slide-a-lyzer cassettes from Pierce. Protein determination of IK (fraction 1) was determined using a Pierce BCA Kit following the manufacturer's instructions.

1.6 Neutralization of Anti-Peptide HVR1 Antibody

In this assay, a constant amount of rAd5 is spiked into diluted serum samples. The spiked serum samples are then added to a monolayer of 293 cells grown on 6 well plates. The "control" consists of 293 cells infected with the rAd5 alone, in the absence of the serum. After a 48 hours infection, the cells are trypsinized, washed and permeabilized, and bound to a FITC labeled antibody to rAd5 hexon. The cell suspension is passed through a Flow Cytometer, and the fraction of fluorescent cells is enumerated. The spiked rAd5 in each sample infects the 293 cells and produce high levels of hexon protein. This protein will bind to the antibody and yield a positive fluorescent signal in the Cytometer. The more infectious virus present in the samples, correlates with a greater # of fluorescing cells. Therefore, a sample containing SNFs to rAd5 will inhibit the infectivity and thus reduce the number of positive fluorescing cells compared to control. A series of dilutions of each serum sample was used and the dilution that gives 50% fluorescence compared to control determines the titer of the SNFs in the serum sample.

1.7 Immune Serum Preparation

Rabbits, pigs and rats were immunized with a highly purified, non-replicating rAd5 (Schering-Plough, Kenilworth, N.J.). Two Yorkshire pigs were immunized subcutaneously every four weeks with 200 μg of rAd5 in 1.0 ml of RIBI adjuvant (RIBI Biologicals) as a primary boost followed by maintenance boosts of 100 μg of rAd5 in 1.0 ml of RIB thereafter every month for several years. The six Sprague Dawley rats and two NZW rabbits were immunized subcutaneously every 3 weeks. The rats received a primary boost of 50 μg of rAd5 in 0.5 ml RIBI followed by maintenance boosts of 10 μg rAd5 in 0.5 ml RIBI. The rabbits received 25 μg of rAd5 in 1.0 ml RIBI boosts throughout. Production bleeds were collected seven days post immunization for all animals. Animals were maintained and procedures preformed by Covance Research Products located in Denver, Pa.

1.8 Protocol for rAd5 Administration to Pigs and Humans

A total of six immune Yorkshire pigs received multiple subcutaneous and repeated intradermal injections of rAd5 for eight weeks. Cancer patients were administered rAd5 based on the type of cancer and the location of the tumor. All patients received at least $7.5 \times 10^8$ particles of rAd5 per dose. Patients with Hepatocellular Carcinoma were administered a single dose of by percutaneous hepatic artery catheter over a 10 minute period. Patients with malignant head and neck cancer, breast cancer and non-small cell lung cancer received a single intratumoral injection. Cancer patients with peritoneal carcinomatosis from ovarian tumors received a single intraperitoneal instillation over 20 minutes. Serum samples were collected at the indicated time points for analysis.

1.9 ELISA Procedure for Anti-rAd5 Antibodies

Anti-rAd5 antibodies were measured using a sandwich ELISA. Prior to the two-day sandwich ELISA, rAd5 (Schering-Plough, Kenilworth, N.J.) was coated onto microtiter plates overnight and then plates were blocked with bovine serum albumin (BSA). The presence of antibodies directed against rAd5 in pig serum samples or human serum was detected by first diluting the controls and unknown samples 1:40 into phosphate buffered saline (PBS) containing 1% BSA on the plate containing the immobilized rAd5. The samples are then diluted serially 2-fold down the plate. After an overnight incubation, unreacted material was removed by washing the plates and a biotin-labeled Protein A/G conjugate was added for 2 hours and then the unbound conjugate was removed by washing. Horseradish peroxidase (HRP) conjugated streptavidin was then added for 2 hours. The bound HRP-conjugate was quantitatively measured after addition of the enzyme's substrate, TMB (3,3',5,5' tetramethyl benzidine). The amount of antibody against rAd5 is proportional to the intensity of the colored end product of the enzymatic reaction. Samples are considered positive for the presence of antibodies to rAd5 if the mean of the sample O.D./NPS O.D. is ≧0.1 for pig samples (established during assay validation) and O.D./NHS O.D. is ≧0.28 for human samples. In addition, samples were considered positive for development of antibodies after treatment with rAd5 if the mean O.D. of the post-dose sample was ≧2-fold the mean O.D. from the pre-dose sample obtained from the same pig or human serum sample.

2.0 Bioassay for Serum Neutralizing Factors

Serum neutralizing antibodies (SNF) to a rAd5 were determined by using a SaOS-2 anti-proliferation assay. In this assay, the rAd5 vector expresses a p53 protein, a critical checkpoint in cell cycle regulation. The absence or mutation of p53 protein impairs the cell's ability to regulate proliferation resulting in uncontrolled growth. The SaOS-2 cell line (human osteogenic sarcoma) lacks the p53 gene. Infection of SaOS-2 cells with rAd5 expressing p53 results in the inhibition of cell growth. The presence of SNFs will lead to a reduction in the degree of p53-induced inhibition of SaOS-2 proliferation. This is measured as a reduction in anti-proliferation activity of rAd5 spiked into a serum sample resulting in a shift of a dose response curve. The cellular response is monitored using the tetrazolium salt MTT, which is metabolized to formazan, solublized with sodium dodecyl sulfate (SDS) and then measured spectrophotometrically.

The observed optical density is related to log cell concentration. Neutralization activity of a serum sample is calculated by comparing the dilution corresponding to 50% maximal inhibition of SaOS-2 cell proliferation of a sample spiked with a standard amount of rAd5 to the dilution corresponding to 50% maximal inhibition of SaOS-2 cell proliferation by a standard amount of rAd5 in the absence of sample. Sample results were expressed as % control. Sample results greater than 85% of control were considered negative for SNF and sample results less than 85% were reported as positive for SNF.

TABLE 1

Amino acid sequences of the seven peptides. Each peptide contains a common amino terminus cysteine residue directly followed by a KGKG (SEQ ID NO:16) linker. The remaining amino acid sequences correspond to the seven unique hypervariable regions (HVR) of adenovirus type 5 (Ad5) hexon.

| Peptide Designation | Amino acid sequence corresponding to Ad5 hexon | |
|---|---|---|
| HVR1 | 137                                      168<br>CKGKGAATALEINLEEEDDDNEDEVDEQAEQQKTHVF | (SEQ ID NO:9) |
| HVR2 | 185       197<br>CKGKGIGVEGQTPKYADK | (SEQ ID NO:10) |
| HVR3 | 210       225<br>CKGKGYETEINHAAGRVLKK | (SEQ ID NO:11) |
| HVR4 | 247       260<br>CKGKGGILVKQQNGKLESQ | (SEQ ID NO:12) |
| HVR5 | 267       283<br>CKGKGSTTEATAGNGDNLTPKV | (SEO ID NO:13) |
| HVR6 | 302       315<br>CKGKGMPTIKEGNSRELMG | (SEQ ID NO:14) |
| HVR7 | 421                                  438<br>CKGKGVINTETLTKVKPKTGQENGWEKDATEFSDK | (SEQ ID NO:15) |

TABLE 2

Antiserum Reactivity to Immomilized Peptides from Pig, Rat, and Rabbit Immunized with rAd5

| | | | Biosensor results in Response units (RU) | | | | | | |
|---|---|---|---|---|---|---|---|---|---|
| Animal I.D. | Timepoint | Peptide: | HVR1 | HVR2 | HVR3 | HVR4 | HVR5 | HVR6 | HVR7 |
| PIG | | | | | | | | | |
| Ozzie | Pre | | 3 | 4 | 3 | 3 | 3 | 3 | 4 |
| Ozzie (6 months post) | post | | 456 | 141 | 209 | 578 | 212 | 143 | 205 |

TABLE 2-continued

Antiserum Reactivity to Immomilized Peptides from Pig, Rat, and Rabbit Immunized with rAd5

| Animal I.D. | Timepoint | Peptide: | HVR1 | HVR2 | HVR3 | HVR4 | HVR5 | HVR6 | HVR7 |
|---|---|---|---|---|---|---|---|---|---|
| RAT | | | | | | | | | |
| Normal rat serum (NRS) | NRS | | 47 | | 44 76 | 46 | 60.5 | 36 | 34 |
| Pooled rat serum from six rats (12 month post) | post | | 456 | | 25 105 | 357 | 24 | 87 | 215 |
| RABBIT | | | | | | | | | |
| Normal rabbit serum (NRbS) | NRbs | | 9 | | 7.5 ND | 6.8 | 5.5 | ND | ND |
| Rabbit 504 (17 months post) | post | | 754 | | 46 115 | 204 | 47 | 92 | 636* | pre = pre-dosed sample
post = post-dosed sample
ND = Not Determined
D = Day after dosing
*Although there is no data for NRbs, the sample was considered positive due to strong reactivity.
Positive results are indicated in Bold based on the following ratio: RU of post sample/RU of pre, NRS or NRbs sample ≧2.0

TABLE 3

Reactivity of Human Clinical samples from Study C95-178 to Immobilized Peptides

| Patient Initials | Timepoint | Peptide: | HVR1 | HVR2 | HVR3 | HVR4 | HVR5 | HVR6 | HVR7 |
|---|---|---|---|---|---|---|---|---|---|
| ER | PRE | | 19 | 19 | 38.4 | 14.1 | 22.1 | 21.9 | 28 |
| | D7 | | ND | ND | ND | ND | ND | ND | ND |
| | D14 | | 26.2 | 27.3 | 41 | 21.1 | 28.7 | 24 | 31 |
| | D21 | | 20.9 | 22.3 | 37 | 17.1 | 17.8 | 21 | 27 |
| FH | PRE | | 23.6 | 26.9 | 49.8 | 25.3 | 26.1 | 72.5 | 29.8 |
| | D3 | | 21 | 21 | ND | 27 | 22.5 | ND | ND |
| | D7 | | 386 | 17.3 | ND | 20.4 | 15.5 | ND | ND |
| | D14 | | 1161 | 34.2 | 54.6 | 33.9 | 36.8 | 82.7 | 32.1 |
| | D21 | | 844.9 | 32.7 | 47.8 | 29.3 | 33.9 | 68 | 25 |
| IK | PRE | | 24.2 | 19.9 | 37.4 | 12.4 | 28 | 17 | 21.3 |
| | D7 | | 2045 | 13.7 | ND | 41.6 | 15 | ND | ND |
| | D14 | | 8266 | 25.3 | 37.4 | 100.6 | 24.6 | 17 | 21.3 |
| | D21 | | 7549 | 13 | ND | 61 | 9 | ND | ND |
| | D28 | | 8385 | 29 | 38.9 | 87.3 | 36.5 | 18.4 | 23 |
| | 2MO. | | 2796 | 10 | ND | 18 | 8.5 | ND | ND |
| HH | PRE | | 32.9 | 20.2 | 60.8 | 19.1 | 22.4 | 38.1 | 51 |
| | D3 | | 30.3 | 13 | ND | 13 | 5 | ND | ND |
| | D7 | | 60.4 | 22 | ND | 22 | 18 | ND | ND |
| | D14 | | 659.6 | 22.6 | 44.6 | 17.4 | 16 | 28.3 | 42.5 |
| | D21 | | 699 | 21.5 | ND | 15 | 9 | ND | ND |
| | D28 | | 433.3 | 25.2 | 41.1 | 17.9 | 20.4 | 27.2 | 38.4 |
| | 2MO. | | 169.8 | 14.9 | ND | 9 | 5 | ND | ND |
| MK | PRE | | 10.8 | 14.2 | 29.1 | 13.1 | 10.9 | 15.2 | 13.2 |
| | D3 | | ND | ND | ND | ND | ND | ND | ND |
| | D7 | | 14.2 | 17.6 | 29.2 | 15.5 | 15.9 | 15.5 | 13.7 |
| SM | PRE | | 23.3 | 23.3 | 37.3 | 16.2 | 31.5 | 16 | 1230 |
| | D6 | | 108 | 20 | 40 | 14.1 | 27.3 | 19.5 | 1026 |
| | D27 | | 173 | 12.3 | 28.6 | 8.6 | 21 | 19 | 522.5 |
| | D48 | | 150.8 | 7.4 | ND | 4.4 | 10.7 | ND | ND |

D = Day
ND = Not Determined
pre = pre-dose

TABLE 4

Reactivity of Commercial Type-Specific Adenovirus Antibodies to Immobilized Peptides

| Vendor | Ab Specificity | Sample I.D. | Peptide: | Biosensor results in Response units (RU) | | | | | | |
|---|---|---|---|---|---|---|---|---|---|---|
| | | | | HVR1 | HVR2 | HVR3 | HVR4 | HVR5 | HVR6 | HVR7 |
| Biogenesis | Goat anti-Ad2 hexon | post | | 25 | 3 | 17 | 3 | 5 | 15 | 15 |
| Accurate | Murine anti-Ad penton (65 KD) | post | | 0 | 0 | 0 | 0 | 0 | 0 | 0 |
| Biodesign | Goat anti-Ad2 hexon | post | | 30 | 10 | ND | 8 | 13 | ND | ND |
| Biospecific | anti-Ad6 | post | | ND | ND | 16 | ND | ND | 10 | 13 |
| Biospecific | anti-Ad3 | post | | ND | ND | 0 | ND | ND | 0 | 0 |
| Lee Biol. | Rabbit anti-Ad5 | pre | | 0 | 0 | 0 | 0 | 0 | 0 | 0 |
| | | post | | 255 | 0 | 6 | 0 | 0 | 8 | 10 | pre = pre-dosed sample
post = post-dosed sample
ND = Not Determined
Positive results are indicated in Bold based on the following criteria:
1) Ratio of RU of post sample/RU of pre sample ≥2.0 OR
2) Post sample (without pre) with a binding greater than 50 RU

TABLE 5

Reactivity of Pre-Clinical Serum Samples to Immobilized Peptides from Pigs that Received rAd5

| Sample I.D. | Timepoint | Peptide: | Biosensor results in Response units (RU) | | | | | | |
|---|---|---|---|---|---|---|---|---|---|
| | | | HVR1 | HVR2 | HVR3 | HVR4 | HVR5 | HVR6 | HVR7 |
| 377 | pre | | 66 | 46 | 101 | 39 | 41 | 87 | 139 |
| 5 | D15 | | 1085 | 58 | 112 | 79 | 58 | 108 | 151 |
| 384 | pre | | 73 | 71 | 99 | 52 | 57 | 98 | 129 |
| 8 | D15 | | 795 | 57 | 87 | 131 | 51 | 70 | 102 |
| 8 | D29 | | 1620 | 65 | 81 | 111 | 62 | 71 | 101 |
| 393 | pre | | 96 | 199 | 83 | 83 | 100 | 65 | 80 |
| 12 | D15 | | 483 | 127 | 71 | 140 | 57 | 95 | 72 |
| 12 | D29 | | 1490 | 107 | 92 | 201 | 63 | 104 | 99 |
| 12 | D48 | | 665 | 113 | 107 | 177 | 94 | 86 | 91 |
| 389 | pre | | 48 | 45 | 73 | 34 | 48 | 69 | 87 |
| 11 | D15 | | 729 | 39 | 52 | 32 | 50 | 53 | 64 |
| 11 | D29 | | 1494 | 61 | 62 | 125 | 68 | 58 | 80 |
| 11 | D48 | | 1024 | 66 | 61 | 136 | 65 | 54 | 84 |
| 390 | pre | | 72 | 80 | 74 | 77 | 73 | 60 | 94 |
| 7 | D15 | | 936 | 64 | 70 | 62 | 56 | 60 | 81 |
| 7 | D29 | | 1200 | 66 | 69 | 75 | 60 | 58 | 76 |
| 385 | pre | | 107 | 80 | 65 | 62 | 72 | 59 | 81 |
| 3 | D15 | | 567 | 49 | 41 | 41 | 42 | 40 | 55 | pre = pre-dose sample
D = Day after dosing
Positive results are indicated in Bold based on the following ratio:
RU of post sample/RU of pre sample ≥2.0

TABLE 6

Reactivity of Serum Samples to Immobilized Peptides from Patients with Non-Small Cell Lung Cancer Administered rAd5

| Patient Initials | Timepoint | Peptide: | Biosensor results in Response units (RU) | | | | | | |
|---|---|---|---|---|---|---|---|---|---|
| | | | HVR1 | HVR2 | HVR3 | HVR4 | HVR5 | HVR6 | HVR7 |
| ER | PRE | | 19 | 19 | 38 | 14 | 22 | 22 | 28 |
| | D7 | | ND | ND | ND | ND | ND | ND | ND |
| | D14 | | 26 | 27 | 41 | 21 | 29 | 24 | 31 |
| | D21 | | 21 | 22 | 37 | 17 | 18 | 21 | 27 |
| FH | PRE | | 24 | 27 | 50 | 25 | 26 | 73 | 30 |
| | D3 | | 21 | 21 | ND | 27 | 23 | ND | ND |
| | D7 | | 386 | 17 | ND | 20 | 16 | ND | ND |
| | D14 | | 1161 | 34 | 55 | 34 | 37 | 83 | 32 |
| | D21 | | 845 | 33 | 48 | 29 | 34 | 68 | 25 |
| IK | PRE | | 24 | 20 | 37 | 12 | 28 | 17 | 21 |
| | D7 | | 2045 | 14 | ND | 42 | 15 | ND | ND |
| | D14 | | 8266 | 25 | 37 | 101 | 25 | 17 | 21 |
| | D21 | | 7549 | 13 | ND | 61 | 9 | ND | ND |

TABLE 6-continued

Reactivity of Serum Samples to Immobilized Peptides from Patients with Non-Small Cell Lung Cancer Administered rAd5

| Patient Initials | Timepoint | Peptide: HVR1 | HVR2 | HVR3 | HVR4 | HVR5 | HVR6 | HVR7 |
|---|---|---|---|---|---|---|---|---|
|  | D28 | 8385 | 29 | 39 | 87 | 37 | 18 | 23 |
|  | 2MO. | 2796 | 10 | ND | 18 | 9 | ND | ND |
| HH | PRE | 33 | 20 | 61 | 19 | 22 | 38 | 51 |
|  | D3 | 30 | 13 | ND | 13 | 5 | ND | ND |
|  | D7 | 60 | 22 | ND | 22 | 18 | ND | ND |
|  | D14 | 660 | 23 | 45 | 17 | 16 | 28 | 43 |
|  | D21 | 699 | 22 | ND | 15 | 9 | ND | ND |
|  | D28 | 433 | 25 | 41 | 18 | 20 | 27 | 38 |
|  | 2MO. | 170 | 15 | ND | 9 | 5 | ND | ND |
| MK | PRE | 11 | 14 | 29 | 13 | 11 | 15 | 13 |
|  | D3 | ND | ND | ND | ND | ND | ND | ND |
|  | D7 | 14 | 18 | 29 | 16 | 16 | 16 | 14 |
| SM | PRE | 23 | 23 | 37 | 16 | 32 | 16 | 1230 |
|  | D6 | 108 | 20 | 40 | 14 | 27 | 20 | 1026 |
|  | D27 | 173 | 12 | 29 | 9 | 21 | 19 | 523 |
|  | D48 | 151 | 7 | ND | 4 | 11 | ND | ND |

D = Day after dosing
ND = Not Determined
pre = pre-dose
MO. = Month's after dosing
Positive results are indicated in Bold based on the following ratio:
RU of post sample/RU of pre sample ≧2.0

TABLE 7

Reactivity of Clinical Samples to Immobilized Peptide from Patients Administered rAd5

| Patient Initials | Timepoint | HVR1 | HVR3 | HVR4 | HVR7 |
|---|---|---|---|---|---|
| A. Patients with Recurrent & Malignant Head and Neck Cancer |
| TGL | PRE | 11 | 32 | 17 | 15 |
|  | D3 | 9 | 24 | 12 | 12 |
|  | D8 | 10 | 29 | 14 | 13 |
|  | D15 | 9 | 27 | 14 | 13 |
|  | D22 | 11 | 31 | 16 | 16 |
|  | D28 | 11 | 29 | 16 | 17 |
| RWT | PRE | 53 | 59 | 27 | 32 |
|  | D3 | 47 | 50 | 23 | 28 |
|  | D10 | 58 | 52 | 28 | 36 |
|  | D14 | 42 | 35 | 17 | 23 |
| B. Patient with Recurrent Melanoma & Breast Cancer |
| ES | PRE | 27 | 27 | 24 | 20 |
|  | D3 | 23 | 26 | 20 | 18 |
|  | D7 | 54 | 27 | 23 | 19 |
|  | D14 | 252 | 28 | 22 | 19 |
|  | D21 | 185 | 28 | 21 | 18 |
|  | D28 | 79 | 15 | 15 | 8 |
| C. Patient with Peritoneal Carcinomatosis |
| VKA | PRE | 7 | 35 | 16 | 12 |
|  | D2 | 10 | 33 | 17 | 16 |
|  | D3 | 8 | 30 | 13 | 17 |
|  | D7 | 14 | 49 | 26 | 17 |
|  | D14 | 41 | 36 | 16 | 29 |
|  | D21 | 45 | 44 | 25 | 26 |
|  | D28 | 38 | 31 | 16 | 25 |
| D. Patients with Hepatocellular Carcinoma |
| JT | PRE | 50 | 206 | 40 | 132 |
|  | D2 | 10 | 33 | 17 | 16 |
|  | D3 | 25 | 136 | 18 | 85 |
|  | D7 | 1629 | 109 | 27 | 73 |
|  | D14 | 7538 | 171 | 108 | 111 |
|  | D21 | 5208 | 187 | 102 | 116 |
|  | D28 | 3837 | 174 | 83 | 108 |
| WMF | PRE | 17 | 24 | 20 | 16 |
|  | D3 | 17 | 23 | 20 | 18 |
|  | D7 | 68 | 18 | 17 | 15 |
|  | D14 | 163 | 27 | 22 | 21 |
|  | D28 | 106 | 19 | 18 | 19 |
| DFB | PRE | 12 | 21 | 13 | 14 |
|  | D3 | 14 | 20 | 14 | 18 |
|  | D7 | 49 | 15 | 12 | 16 |
|  | D14 | 1226 | 26 | 14 | 19 |
|  | D21 | 606 | 22 | 10 | 14 |
|  | D28 | 414 | 32 | 19 | 23 |
| RK | PRE | 21 | 21 | 14 | 19 |
|  | D3 | 19 | 18 | 12 | 19 |
|  | D7 | 40 | 25 | 20 | 25 |
|  | D14 | 113 | 21 | 15 | 18 |
|  | D21 | 75 | 19 | 13 | 19 |
|  | D28 | 88 | 32 | 22 | 32 |

PRE = pre-dose
D = Day after dosing
Positive results are indicated in Bold based on the following ratio:
RU of post sample/RU of pre sample ≧2.0

TABLE 8

Reactivity of pre-clinical swine serum samples from SN 96380 to Immobilized Peptides

| | | | Biosensor results in Response units (RU) | | | | | | |
|---|---|---|---|---|---|---|---|---|---|
| Sample I.D. | Timepoint | Peptide | HVR1 | HVR2 | HVR3 | HVR4 | HVR5 | HVR6 | HVR7 |
| 377 | pre | | 66.4 | 46.2 | 100.8 | 38.9 | 41 | 87.3 | 138.5 |
| 5 | D15 | | 1085 | 57.6 | 111.9 | 79 | 58 | 107.6 | 150.6 |
| 384 | pre | | 73.2 | 71.4 | 98.9 | 52.3 | 57.3 | 97.6 | 129.4 |
| 8 | D15 | | 794.9 | 56.6 | 87 | 130.6 | 50.7 | 70 | 102.3 |
| 8 | D29 | | 1620 | 65 | 81 | 111.4 | 62.3 | 71 | 101 |
| 393 | pre | | 96 | 199 | 83.4 | 83 | 100.4 | 65 | 80 |
| 12 | D15 | | 482.7 | 127 | 71 | 140 | 57.2 | 95 | 72 |
| 12 | D29 | | 1490 | 106.5 | 92 | 200.8 | 63 | 103.5 | 99.1 |
| 12 | D48 | | 664.6 | 113.2 | 106.8 | 176.5 | 94 | 86 | 91 |
| 389 | pre | | 47.7 | 44.6 | 72.5 | 33.5 | 47.9 | 69 | 87 |
| 11 | D15 | | 728.6 | 39 | 52 | 32 | 50 | 52.5 | 64 |
| 11 | D29 | | 1494 | 61.4 | 62 | 124.8 | 68.3 | 58 | 80 |
| 11 | D48 | | 1024 | 65.6 | 61 | 136.2 | 64.9 | 54 | 84 |
| 390 | pre | | 71.6 | 80 | 73.6 | 77.3 | 72.9 | 60 | 94 |
| 7 | D15 | | 936 | 64 | 69.5 | 62 | 55.6 | 60 | 80.5 |
| 7 | D29 | | 1200 | 66.4 | 69 | 75 | 60 | 58 | 76 |
| 385 | pre | | 106.7 | 80 | 65 | 62 | 72 | 59 | 81 |
| 3 | D15 | | 567.4 | 49.1 | 41 | 41 | 42 | 40 | 55 | pre = pre-does sample
D = Day

TABLE 9

C95-177-01 - RECURRENT OR METASTATIC HEAD & NECK CANCER

| INITIALS | SAMPLE | HVR1 | HVR3 | HVR4 | HVR7 |
|---|---|---|---|---|---|
| TGL | PRE | 11.3 | 31.5 | 16.6 | 15.2 |
| | D3 | 8.7 | 23.6 | 12.1 | 12.4 |
| | D8 | 9.5 | 28.9 | 14 | 13.4 |
| | D15 | 9.2 | 27 | 13.6 | 13.3 |
| | D22 | 11 | 30.7 | 16.3 | 15.5 |
| | D29 | 10.9 | 29.3 | 15.6 | 16.6 |
| RWT | PRE | 52.5 | 59 | 26.6 | 31.8 |
| | D3 | 46.8 | 49.8 | 23 | 28.3 |
| | D10 | 58 | 52.3 | 27.9 | 36.3 |
| | D14 | 41.5 | 35 | 17.4 | 22.9 |

I95-082-04 - RECURRENT MELANOMA OR BREAST CANCER

| INITIALS | SAMPLE | HVR1 | HVR3 | HVR4 | HVR7 |
|---|---|---|---|---|---|
| ES | PRE | 27 | 27.4 | 23.5 | 19.8 |
| | D3 | 22.8 | 25.8 | 20.3 | 17.8 |
| | D7 | 53.7 | 27.4 | 23.2 | 19.4 |
| | D14 | 252 | 28.2 | 21.7 | 18.6 |
| | D21 | 185 | 27.6 | 20.8 | 17.7 |
| | D28 | 78.6 | 14.6 | 10 | 8.2 |

C95-084-01- PERITONEAL CARCINOMATOSIS

| INITIALS | SAMPLE | HVR1 | HVR3 | HVR4 | HVR7 |
|---|---|---|---|---|---|
| VKA | PRE | 7.4 | 35 | 16.2 | 12 |
| | D2 | 10.1 | 33 | 16.9 | 15.6 |
| | D3 | 7.7 | 29.7 | 13.1 | 16.5 |
| | D7 | 14 | 48.6 | 26 | 17.4 |
| | D14 | 41 | 36 | 16 | 28.9 |
| | D21 | 44.5 | 43.8 | 25.4 | 26.1 |
| | D28 | 38.1 | 30.6 | 16.3 | 24.7 |

C95-063-01 - HEPATOCELLULAR CARCINOMA

| INITIALS | SAMPLE | HVR1 | HVR3 | HVR4 | HVR7 |
|---|---|---|---|---|---|
| CLL | PRE | 8.3 | 15.9 | 12.6 | 11.7 |
| | D3 | 6.6 | 17.8 | 11.8 | 10.4 |
| JT | PRE | 50.3 | 205.8 | 39.7 | 131.7 |
| | D2 | 10.1 | 33 | 16.9 | 15.6 |
| | D3 | 24.6 | 135.6 | 18 | 85.1 |
| | D7 | 1629 | 108.5 | 26.6 | 72.6 |
| | D14 | 7538 | 170.6 | 108 | 110.6 |
| | D21 | 5208 | 186.5 | 102 | 116.1 |
| | D28 | 3837 | 173.8 | 82.5 | 107.8 |

TABLE 9-continued

| | | | | | |
|---|---|---|---|---|---|
| EL | PRE | 23.4 | 26.6 | 21.4 | 22.4 |
| JK | PRE2 | 21.7 | 33.7 | 20.6 | 33.8 |
| | PRE1 | 17 | 28.8 | 15.9 | 26.5 |
| WMF | PRE | 16.7 | 23.5 | 19.5 | 15.8 |
| | D3 | 17.3 | 22.5 | 19.5 | 17.5 |
| | D7 | 67.7 | 18.3 | 17 | 15.3 |
| | D14 | 163 | 26.8 | 22.3 | 21.4 |
| | D28 | 106 | 19.2 | 17.7 | 18.9 |
| DFB | PRE | 12.3 | 21 | 12.6 | 14 |
| | D3 | 13.7 | 20.3 | 13.9 | 18.1 |
| | D7 | 48.7 | 15.3 | 11.5 | 15.6 |
| | D14 | 1226 | 26.3 | 14.3 | 18.6 |
| | D21 | 606 | 22.3 | 10.4 | 14.2 |
| | D28 | 414 | 32.3 | 19.1 | 22.6 |
| RK | PRE | 20.7 | 20.5 | 14.2 | 19.2 |
| | D3 | 18.5 | 17.5 | 12.4 | 19.4 |
| | D7 | 39.5 | 24.6 | 19.5 | 24.6 |
| | D14 | 113 | 21.2 | 14.9 | 18 |
| | D21 | 75.3 | 19 | 13.1 | 19.3 |
| | D28 | 87.6 | 31.9 | 21.9 | 31.8 |

TABLE 10

Results of Anti-rAd5 Serum Antibody Determined by ELISA,
Bioassay and Biosensor Assay from
Cancer Patients Administered rAd5

| | | | Ratio of # Positive Ab/Total # samples | | |
|---|---|---|---|---|---|
| Cancer Diagnosis | # of Patients | Sample I.D. | ELISA | Bioassay | Biosensor |
| NSCLC | 6 | pre | 6/6 | 5/6 | 0/6 |
| | | post | 4/6 | 1/6 | 4/6 |
| Melanoma and Breast Cancer | 1 | pre | 0/1 | 0/1 | 0/1 |
| | | post | 1/1 | 1/1 | 1/1 |
| Malignant Head and Neck Cancer | 2 | pre | 2/2 | 2/2 | 0/2 |
| | | post | 0/2 | 0/2 | 0/2 |
| Peritoneal Carcinomatosis | 1 | pre | 1/1 | 1/1 | 0/1 |
| | | post | 1/1 | 0/1 | 1/1 |
| Hepatocellular Carcinoma | 4 | pre | 4/4 | 4/4 | 0/1 |
| | | post | 2/4 | 0/4 | 4/4 | pre = pre-dosed sample
post = post-dosed sample
ND = Not Determined
Positive results are indicated in Bold based on the following criteria:
1) Ratio of RU of post sample/RU of pre sample ≧2.0 OR
2) Post sample (without pre) with a binding greater than 50 RU

TABLE 11

Summary of Results for Anti-rAd5 Serum Antibody
Determined by ELISA, Bioassay and Biosensor Assay from
Cancer Patients Administered rAd5

| | # Ab Positive/# samples | | |
|---|---|---|---|
| | ELISA | Bioassay | Biosensor |
| Presence of pre-existing Anti-Ad5 Abs | 14/14 | 12/14 | 0/14 |
| Development of Anti-Ad5 Abs | 7/14 | 2/14 | 10/14 |

ELISA Antigen = rAd5
Biosensor Antigen = specific Ad5 peptides HVR1, 3, 4, and 7
Bioassay = rAd5 infection of cells From the above, it is clear that the present invention provides an efficient method of determining the likelihood that a patient host's immune system will interfere with intended gene therapy using viral vectors.

We claim:

1. A method for detecting an antibody capable of binding to adenovirus in a sample, comprising:
   a) immobilizing a peptide comprising an amino acid sequence selected from the group consisting of SEQ ID NOs: 9, 12 and 15 onto a flowcell of a sensorchip in a biosensor;
   b) contacting the sample with the immobilized peptide; and
   c) detecting binding of the antibody to the immobilized peptide by detecting surface plasmon resonance in the biosensor.

2. The method of claim 1, wherein the adenovirus is adenovirus 5.

3. The method of claim 1, wherein said sample is human serum.

4. The method of claim 1, wherein a plurality of peptides capable of being bound by an anti-adenovirus antibody are directly immobilized, each on its own separate flowcell, and wherein at least one peptide of the plurality comprises an amino acid sequence selected from the group consisting of SEQ ID NOs: 9, 12 and 15.

5. A method for detecting an antibody capable of binding to adenovirus in a sample, comprising:
   a) immobilizing a peptide comprising an amino acid sequence selected from the group consisting of SEQ ID Nos: 9, 12 and 15 onto a solid support;
   b) contacting the peptide with the sample;
   c) labeling the antibody which binds to the peptide; and
   d) detecting the labeled antibody.

6. The method of claim 5, wherein the labeled antibody in step (d) is detected by steps comprising:
   i) labeling said antibody with a biotin-labeled Protein A/G conjugate;
   ii) contacting the biotin-labeled Protein A/G conjugate with horseradish peroxidase (HRP-conjugated streptavidin;
   iii) contacting the HRP-conjugated streptavidin with 3,3', 5,5' tetramethyl benzidine;
   iv) producing a colored end product; and
   v) measuring the intensity of the colored end product.

7. The method of claim 5, wherein the sample is contacted with a plurality of peptides, wherein at least one peptide of the plurality comprises an amino acid sequence selected from the group consisting of SEQ ID NOs: 9, 12 and 15.

8. The method of claim 5, wherein the sample is human serum.

9. The method of claim 5, wherein the adenovirus is adenovirus 5.

* * * * *